(12) United States Patent
Williams

(10) Patent No.: US 9,012,226 B2
(45) Date of Patent: Apr. 21, 2015

(54) BACTERIAL STRAINS WITH IMPROVED PLASMID STABILITY

(75) Inventor: James A. Williams, Lincoln, NE (US)

(73) Assignee: Nature Technology Corporation, Lincoln, NE (US)

( * ) Notice: Subject to any disclaimer, the term of this patent is extended or adjusted under 35 U.S.C. 154(b) by 597 days.

(21) Appl. No.: 12/659,464

(22) Filed: Mar. 10, 2010

(65) Prior Publication Data

US 2010/0233814 A1    Sep. 16, 2010

Related U.S. Application Data

(60) Provisional application No. 61/210,073, filed on Mar. 13, 2009.

(51) Int. Cl.
C12N 15/70 (2006.01)
C12N 15/74 (2006.01)
C12P 21/00 (2006.01)

(52) U.S. Cl.
CPC ............................... *C12N 15/74* (2013.01)

(58) Field of Classification Search
None
See application file for complete search history.

(56) References Cited

U.S. PATENT DOCUMENTS 6,881,558 B1    4/2005    Weiner et al.

FOREIGN PATENT DOCUMENTS

WO    WO 2008/153733    12/2008
WO    WO 2009/025690    2/2009

OTHER PUBLICATIONS

Kim and Cha (Biotechnology and Bioengineering, 2003. vol. 83, pp. 841-853).*
Haldimann and Wanner (Journal of Bacteriology, 2001. vol. 183, pp. 6384-6393).*
Engels P., et al., 1993, Biotechniques 14: 324-325.
Brosius J., 1984, Gene, 27: 161-172.
Chen W., et al., 1993, Gene 130: 15-22.
Chen JD., et al., 1987, Gene 55: 179-187.
Saida F., et al., 2006, Current Protein Peptide Science 7: 47-56.
Boyd A.C., et al., 1999, J. Gene Med. 1: 312-321.
Futterer, J., et al., 1988, Gene 67: 141-145.
Love, C.A. et al., 1996, Gene 176: 49-53.
Kemmer, C., et al., 2006, *Microbial Cell Factories* 5: 38.
Coleman, J., et al., 1984, *Cell* 37: 429-436.
Datsenko, K.A., et al., 2000, *Proc Natl. Acad. Sci. USA* 97: 6640-6645.
Lissemor, J.L., et al., 2000, *Biotechniques* 28: 83-89.
Makrides, S.C., 1996, *Microbiol. Rev.* 60: 512-538.
Lee, L.K., et al., 2003, *Current Opinion Biotechnology* 14: 505.
Rasmussen, L.C.V., et al., 2007, *Microbial Cell Factories* 6: 24.

\* cited by examiner

*Primary Examiner* — Celine Qian
(74) *Attorney, Agent, or Firm* — Brooks Kushman P.C.

(57) ABSTRACT

The present invention relates to the propagation of covalently closed circular recombinant DNA molecules such as plasmids, cosmids, bacterial artificial chromosomes (BACs), bacteriophages, viral vectors and hybrids thereof, and more particularly is strain modifications that improve strain viability, plasmid stability, plasmid production yield, and plasmid-directed protein production yield, using said DNA molecules in fermentation culture.

5 Claims, 5 Drawing Sheets

BACTERIAL STRAINS WITH IMPROVED PLASMID STABILITY

CROSS REFERENCE TO RELATED APPLICATIONS

This application claims priority to U.S. Provisional Patent Application Ser. No. 61/210,073, entitled "Bacterial Strains with Improved Plasmid Stability" which was filed Mar. 13, 2009, the entire contents of which are incorporated herein by reference.

STATEMENT REGARDING FEDERALLY SPONSORED RESEARCH OR DEVELOPMENT

This invention was supported in part with government support under Grant No. 2 R44 GM072141-02, awarded by the National Institutes of Health. The government has certain rights in this invention.

FIELD OF THE INVENTION

The present invention relates to the propagation of covalently closed circular recombinant DNA molecules such as plasmids, cosmids, bacterial artificial chromosomes (BACs), bacteriophages, viral vectors and hybrids thereof, and more particularly is strain modifications that improve strain viability, plasmid stability, plasmid production yield, and plasmid-directed protein production yield, using said DNA molecules in fermentation culture. Such recombinant DNA molecules are useful in biotechnology, transgenic organisms, gene therapy, therapeutic vaccination, agriculture and DNA vaccines.

BACKGROUND OF THE INVENTION

E. coli plasmids have long been an important source of recombinant DNA molecules used by researchers and by industry. Therapeutic plasmids and plasmid based bacterial expression vectors typically contain a pMB1, ColE1 or pBR322 derived replication origin. In general, the replication origin needs to be protected from read-through transcription from adjacent genes, for example from cryptic promoters in an antigen gene insert, to prevent plasmid destabilization or reduced copy number (Engels P, Meyer P. 1993. Biotechniques 14: 324-5). This may be accomplished by inclusion of shielding transcriptional terminators. For example, transcriptional terminators shielding the prokaryotic replication origin from insert mediated transcriptional read-through reduce insert toxicity due to eukaryotic gene transcription (Brosius J. 1984. Gene, 27: 161-72; Chen W, Kallio P T, Bailey J E. 1993. Gene 130: 15-22; Chen J D, Morrision D A. 1987. Gene 55: 179-87).

However, a gene insert may contain DNA structures, proteins or peptides that are toxic to the host cell. Hydrophobic membrane spanning peptides are particularly toxic to bacteria. Expression of these peptides, by gene insert containing cryptic bacterial promoters or vector encoded cryptic bacterial promoters, will not be prevented by transcriptional terminators shielding the prokaryotic replication origin.

Translation of an insert encoded sense strand toxic peptide may be prevented by introduction of a reverse oriented promoter after the insert, to generate translation-disrupting antisense RNA (Weiner D B, Zhang D, Cohen A. 2005. U.S. Pat. No. 6,881,558; reviewed by Saida F, Uzan M, Odaert B, Bontems F. 2006. Current Protein Peptide Science 7: 47-56). This has the disadvantage of requiring vector modification to insert the promoter. As well, since not all insert borne toxic peptides are expressed from the sense strand, this strategy will detrimentally increase expression of toxic peptides encoded by the antisense strand.

Alternatively, stabilization of a plasmid containing an insert encoded toxic peptide may be achieved through insertion of an intron to disrupt bacterial production of a known toxic protein (Boyd A C, Popp F, Michaelis U, Davidson H, Davidson-Smith H, Doherty A, McLachlan G, Porteous D J, Seeber S. 1999. J. Gene Med. 1: 312-21). This method has the disadvantage of requiring vector modification to insert the intron, and requires knowledge of both the exact location of the toxic peptide, as well as a site within this toxic peptide in which insertion of an intron will disrupt toxicity.

Alternatively, stabilization of a plasmid containing an insert encoded toxic peptide may be achieved through expression of antisense RNA from a second plasmid. The antisense RNA from the second plasmid will bind to the mRNA encoding the toxic peptide (Futterer J, Gordon K, Pfeiffer P, Hohn T. 1988. Gene 67: 141-5). A disadvantage of this strategy is required dual selection for two plasmids, and two plasmids containing identical inserts would likely recombine (Weiner et al., Supra, 2005). As well, for plasmid production, contamination of the target plasmid with the antisense-RNA encoding second replicon would be unacceptable. The increased metabolic burden associated with maintaining a second plasmid is also undesired.

Even in view of the prior art there is a need to reduce insert-associated toxicity, to prevent plasmid destabilization or reduced copy number that would affect plasmid production, or plasmid directed protein production.

SUMMARY OF THE INVENTION

The present invention relates generally to methods of increasing production yield of covalently closed super-coiled plasmid DNA. The invention can be practiced to improve the copy number of vectors such as bacterial expression vectors useful for manufacturing proteins or metabolites in bacteria, or eukaryotic expression plasmids useful for gene therapy, genetic immunization and or recombinant protein expression.

One object of the invention is to provide methods for reducing plasmid insert-associated toxicity, to prevent plasmid destabilization or reduced copy number.

According to one object of the invention a method to reduce insert-associated toxicity is provided, to prevent plasmid destabilization or reduced copy number.

According to another object of the invention, an RNA expression vector is incorporated into the bacterial genome.

According to another object of the invention, the RNA expression vector directs expression of a DNA fragment corresponding to part, or all, of the insert region of a plasmid requiring stabilization and/or increased copy number. Expression of the chromosomal copy of the insert reduces insert-associated plasmid toxicity, preventing plasmid destabilization or reduced copy number.

According to another object of the invention, the RNA expression vector expresses the sense strand of the DNA fragment of the insert region of the plasmid requiring stabilization and increased copy number.

According to another object of the invention, the RNA expression vector expresses the antisense strand of the DNA fragment of the insert region of the plasmid requiring stabilization and increased copy number.

Further objects and advantages of the invention will become apparent from a consideration of the drawings and ensuing description.

DETAILED DESCRIPTION OF THE PREFERRED EMBODIMENTS

The inventions relates generally to methods for stabilizing and improving the copy number of vectors. The invention can be practiced to stabilize and improve the copy number of vectors such as bacterial expression vectors useful for protein production, or eukaryotic expression plasmids useful for gene therapy, genetic immunization and or recombinant protein production. It is to be understood that all references cited herein are incorporated by reference, in their entirety.

According to one preferred embodiment, the present invention provides for a method of increasing copy number of covalently closed super-coiled plasmid DNA, which comprises modifying the host strain to express an insert-complementary RNA from the bacterial genome.

In one preferred embodiment, the method of increasing copy number of covalently closed super-coiled plasmid DNA comprises modifying the host strain to express an RNA from the bacterial genome that is complementary to the sense strand of the insert.

In one preferred embodiment, the method of increasing copy number of covalently closed super-coiled plasmid DNA comprises modifying the host strain to express an RNA from the bacterial genome that is complementary to the antisense strand of the insert.

According to one preferred embodiment, the bacterial host is the gram negative bacterium *E. coli*.

The methods of strain modification of the present invention have been surprisingly found to improve plasmid yield in subsequent shake flask and or fermentation culture.

Figure 1:
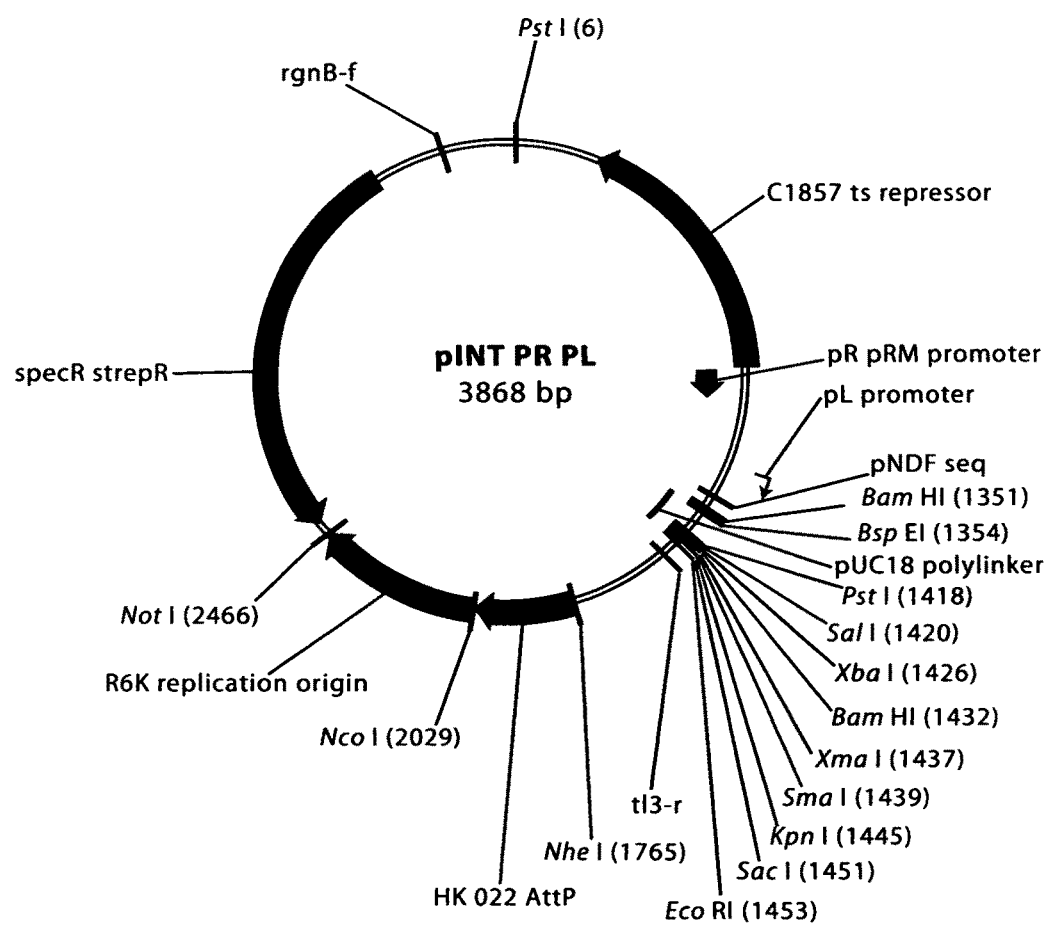
FIG. 1 depicts the pINT PR PL vector.

Turning now to the drawings, FIG. 1 shows an annotated map of the pINT PR PL vector with the locations of the R6K replication origin, spectinomycin/streptomycin resistance marker (specR/strepR), phage HK022 AttP attachment site for genome integration, phage $\lambda p_R$-$\lambda p_L$ promoters and C1857ts λ repressor, pUC18 polylinker, and rgnB-f and tL3-r sequencing primers indicated.

Figure 2:
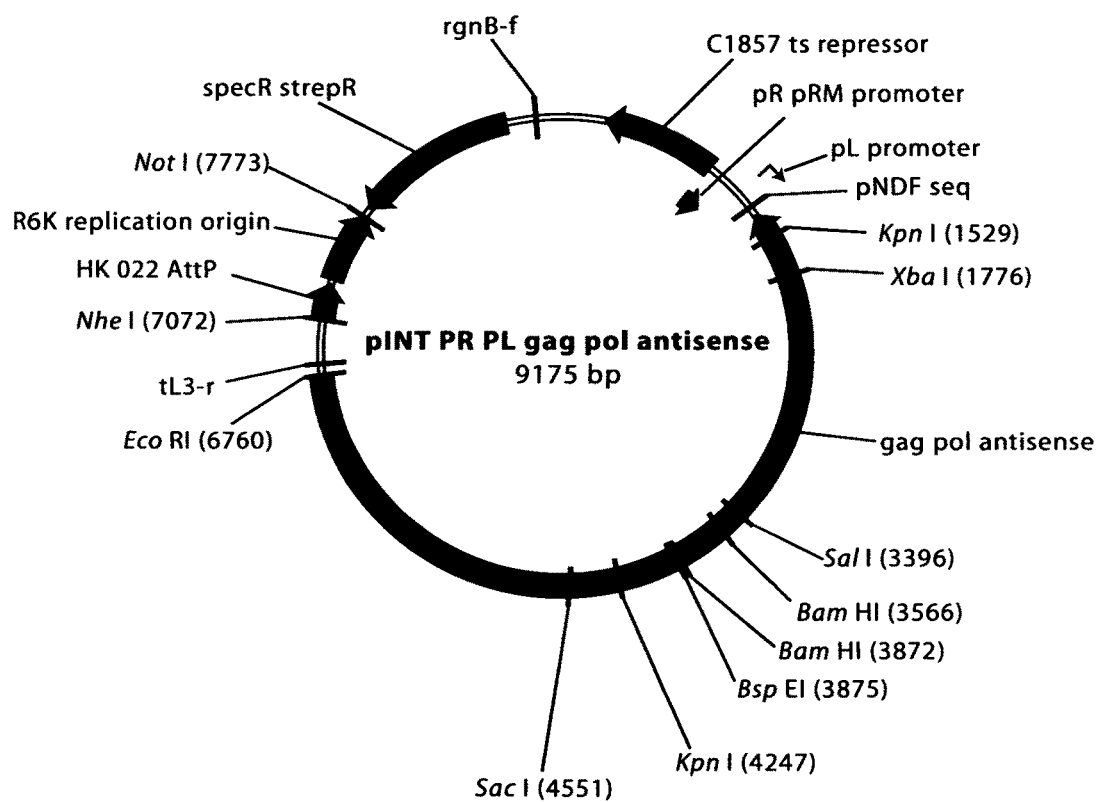
FIG. 2 depicts the pINT PR PL gag pol antisense vector.

FIG. 2 shows the pINT PR PL gag pol antisense vector, with the locations of the gag pol genes (in antisense orientation), the R6K replication origin, spectinomycin/streptomycin resistance marker (specR/strepR), phage HK022 AttP attachment site for genome integration, phage $\lambda p_R$-$\lambda p_L$ promoters and C1857ts λ repressor, pUC18 polylinker, and rgnB-f and tL3-r sequencing primers indicated.

Figure 3:
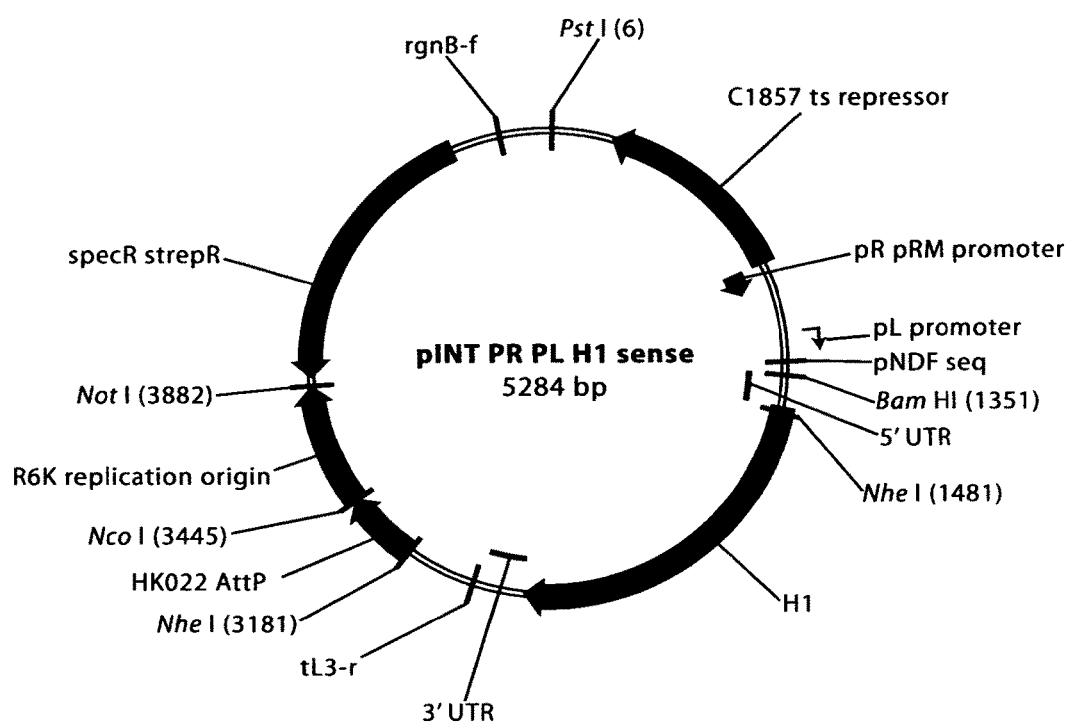
FIG. 3 depicts the pINT PR PL HI sense vector.

FIG. 3 shows the pINT PR PL HI sense vector with the locations of the influenza H1 hemagglutinin gene (in sense orientation), the R6K replication origin, spectinomycin/streptomycin resistance marker (specR/strepR), phage HK022 AttP attachment site for genome integration, phage $\lambda p_R$-$\lambda p_L$ promoters and C1857ts λ repressor, pUC18 polylinker, and rgnB-f and tL3-r sequencing primers indicated.

Figure 4:
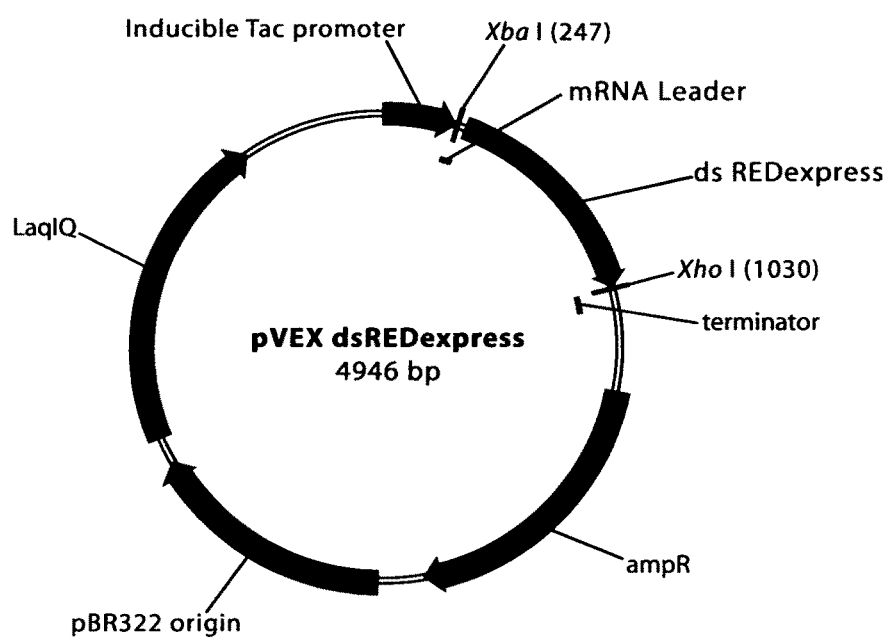
FIG. 4 depicts the pVEX DSREDExpress expression vector.

FIG. 4 shows the pVEX DSREDExpress expression vector with the locations of the pBR322 replication origin, the LacIq repressor, the LaqIq regulated inducible tac promoter, the transcribed mRNA leader, the translated DsRedexpress gene, the transcriptional terminator, and the ampicillin resistance (ampR) marker indicated.

Figure 5:
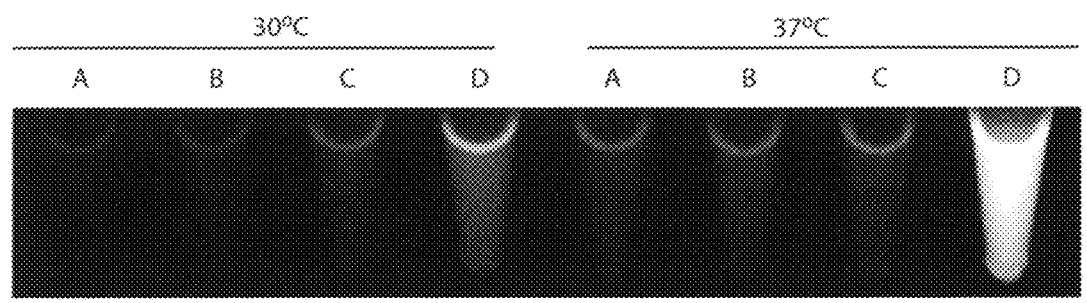
FIG. 5 illustrates chromosomal antisense silencing of pVEX-DSREDExpress uninduced expression.
Table 1. 30° C. constant temperature 10 L fed-batch fermentations with pMLV gag pol vector
Table 2. 30° C.-42° C. temperature induced 10 L fed-batch fermentations with NTC7382 41H H1 HA
SEQ ID NO:1: pINT PR PL vector
Definition of Terms
amp: Ampicillin
ampR: Ampicillin resistance
Bacterial genome: Chromosome or F factor of gram negative or gram positive bacteria such as *Pseudomonas, Salmonella, Escherichia, Bacillus, Clostridia* or other species
Bacterial host: Gram negative or gram positive bacteria such as *Pseudomonas, Salmonella, Escherichia, Bacillus, Clostridia* or other species
bp: basepair
DNA replicon: Plasmids, cosmids, bacterial artificial chromosomes (BACs), bacteriophages, viral vectors and hybrids thereof
*E. coli*: *Escherichia coli*, a gram negative bacteria
Expression vector: A plasmid that is used to express one or more genes in a eukaryotic and or prokaryotic target cell
F factor: Fertility Factor. For example, the *Escherichia coli* conjugative plasmid
HA: Hemagglutinin
kan: kanamycin
kanR: kanamycin resistance
kb: kilobase
MuLV: Murine Leukemia Virus
$OD_{600}$: Optical density at 600 nm
PCR: Polymerase Chain Reaction
Plasmid: An extra-chromosomal DNA molecule which can replicate independently of the chromosomal DNA
pUC origin: pBR322-derived origin, with G to A transition that increases copy number at elevated temperature
pUC plasmid: Plasmid containing the pUC origin
RNA expression vector: Expression vector that expresses RNA constitutively or conditionally in a prokaryotic or eukaryotic target cell
UTR: Untranslated region flanking a mRNA coding region. The 5' side flanking sequence is called the 5' UTR while the 3' flanking sequence is called the 3' UTR
vector: A gene delivery vehicle, including viral (e.g. alphavirus, poxvirus, lentivirus, retrovirus, adenovirus, adenovirus related virus, etc) and nonviral (e.g. plasmid, midge, transcriptionally active PCR fragment, minicircles, bacteriophage, etc) vectors. These are well known in the art and are included herein by reference.

FIG. 5 demonstrates chromosomal expression of antisense RNA complementary to the pVEX dsREDexpress insert eliminates uninduced leaky dsREDexpress expression. Fluorescence of soluble cell lysates from: A) DH5α; B) DH5α-Antisense; C) DH5α-Antisense+pVEXDsREDExpress; D) DH5α+pVEXDsREDExpress after growth in LB media at 30° C. or 37° C. DH5α-Antisense is the DH5α–pINT PR PL DsREDExpress antisense cell line.

We disclose herein the surprising observation that an insert complementary RNA expressed from the genome can be utilized to stabilize plasmids and improve copy number.

EXAMPLES

The methods of the invention are further illustrated by the following examples. These are provided by way of illustration and are not intended in any way to limit the scope of the invention.

Example 1

Development of Vectors Expressing Anti-Insert RNA

A number of vectors contain insert sequences that dramatically reduce vector yield and stability for unknown reasons. The inserts from two poor producing plasmid vectors (pMLV gag pol, and NTC7382 41H H1 HA) were cloned into an RNA expression vector as described below.

pINT PR PL vector

The pINT PR PL vector is a replication incompetent plasmid that may be site specifically integrated into the genome at the HK022 bacteriophage attachment site utilizing HK022 bacteriophage recombinase-expressing plasmid pAH69 (Haldimann A, Wanner B L. 2001. J Bacteriol. 183: 6384-6393). The pINT PR PL plasmid is a derivative of pAH144 (Haldimann and Wanner, Supra, 2001). The pAH144 plasmid contains the R6K conditional replication origin and requires an engineered pir+host cell strain such as BW23474 for propagation. This origin is non functional in most strains including DH5α. The vector also contains a multiple cloning site, a streptomycinR and spectinomycinR resistance marker (spec/strep) and the HK022 attachment site. pAH144 and pAH69 were obtained from the E. coli genetic stock center (New Haven, Conn.).

The pND213 (Love C A, Lilley P E, Dixon N E. 1996. Gene 176:49-53) native stuffer protein expression vector was digested with BamHI/PstI and the 1.35 kb fragment containing the phage lambda C1857ts λ repressor, $λp_R$-$λp_L$ promoters upstream of a multiple cloning site was purified. pAH144 was digested with BamHI/PstI and the linear vector (2.45 kb) was purified. The two fragments were ligated and transformed into the BW23474 cell line. Recombinants (pAH144-lambda repressor) were selected on spec/strep, concentration 35 ug/mL each, and confirmed by restriction digestion and sequencing with the RgnB-f and tL3-r primers described in Haldimann and Wanner, Supra, 2001. This vector was digested with BamHI (sticky end filled using klenow enzyme) and EcoRI to remove the ribosome binding site, and the pUC18 polylinker (encoded in a 102 by BsrBI/EcoRI fragment) added by ligation. The final vector (pINT PR PL; FIG. 1; SEQ ID NO:1) was sequenced confirmed. This vector can overproduce target RNA at low levels at 30° C. (repressed) and much higher levels after 37-42° C. temperature induction mediated inactivation of the C1857ts lambda repressor.

pMLV gag pol

This is an 11 kb ampicillin resistant (ampR) helper plasmid containing the CMV promoter driven MuLV gag pol genes. Helper plasmids containing MuLV gag pol genes are used to manufacture retroviruses. The plasmids are transfected into cell lines, and produce gag pol enzymes necessary for retroviral packaging. However, gag pol plasmids are often toxic; improving plasmid yields would be valuable to enable economical helper plasmid production.

pINT PR PL gag pol antisense vector

A derivative of pAH144-lambda repressor containing a 5.4 kb SmaI-EcoRI DNA fragment from pMLV gag pol that encodes the murine leukemia virus (MuLV) gag pol genes replacing the BamHI (filled with klenow)-EcoRI polylinker of the pINT PR PL vector (FIG. 2). The gag pol genes are inserted in the antisense orientation.

NTC7382 41H H1 HA

The kanamycin resistant (kanR) NTC7382 41H HA vector containing influenza serotype H5 hemagglutinin (HA) was disclosed in Williams 2008 WO 2008/153733 and is included herein by reference. The NTC7382 41H H1 HA vector is a modified vector with a poor-yielding influenza serotype H1 hemagglutinin gene substituted for H5 HA.

pINT PR PL H1 sense vector

A derivative of pAH144-lambda repressor containing a 1.8 kb BamHI-StuI DNA fragment that encodes the influenza serotype H1 HA gene and flanking 5' UTR and 3' UTR replacing the BamHI-EcoRI (both sites filled with Klenow) polylinker of the pINT PR PL vector (FIG. 3). The H1 HA gene is inserted in the sense orientation.

Example 2

Creation and Evaluation of Cell Lines Expressing Anti-Insert RNA

Cell lines were constructed with a single copy of the insert containing RNA expression vector integrated into the genome. The poor producing plasmid was then transformed into the RNA expression vector cell line and plasmid yield from the modified cell line, compared to the parent cell line, assessed in fermentation culture.

Manufacturing cell lines: Fermentations were performed with E. coli strain DH5α [F–Φ80d/acZΔM15 Δ(lacZYA-argF) U169 recA1 endA1 hsdR17(rk–, mk+) phoA supE44 λ-thi-1 gyrA96 recA1] or DH5α–pINT PR PL H1 sense or DH5α–pINT PR PL gag pol antisense. The latter two cell lines contain a single copy of the indicated pINT PR PL plasmid integrated into the genome at the HK022 bacteriophage attachment site utilizing HK022 bacteriophage recombinase-expressing plasmid pAH69, and single copy integrants confirmed with PCR using P1-P4 primers as described (Haldimann and Wanner Supra. 2001). The helper plasmid was removed, and the corresponding test plasmid was transformed into the cell line and seed stock manufactured as described in Carnes A E, Williams J A. Hodgson C P. 2009 WO 2009/025690, included herein by reference.

Fermentation: Fermentations were performed using proprietary fed-batch media (NTC3019) in New Brunswick Bio-Flo 110 bioreactors as described (Carnes et al., Supra, 2009). The seed cultures were started from glycerol stocks and streaked onto LB medium agar plates containing 50 µg/mL kanamycin (NTC7382 41H H1 HA) or 100 µg/mL ampicillin (pMLV gag pol). The plates were grown at 30° C., cells were resuspended in media, and used to provide approximately 0.1% inoculums for the fermentations.

Analytical Methods: Culture samples were taken at key points and at regular intervals during all fermentations. Samples were analyzed immediately for biomass ($OD_{600}$) and for plasmid yield. Plasmid yield was determined by quantification of plasmid obtained from Qiagen Spin Miniprep Kit preparations as described (Carnes et al., Supra, 2009). Briefly, cells were alkaline lysed, clarified, plasmid was column purified, and eluted prior to quantification. Agarose gel electrophoresis analysis was performed on 0.8-1% Tris/acetate/EDTA (TAE) gels as described in Carnes et al., Supra, 2009.

Example 3

Host Strain Producing Antisense RNA Complementary to the MuLV Gag Pol Gene Insert Improved Toxic Plasmid pMLV Gag Pol Yield Triplicate fermentations of the DH5α antisense (DH5α–pINT PR PL gag pol antisense) pMLV gag pol cell line at 30°

C. constant temperature resulted in very high plasmid specific yield (5.0 to 6.7 specific yields at harvest; Table 1). A fermentation of the control DH5α:pMLV gag pol strain at 30° C. constant temperature had much lower copy number (0.9 specific yield at harvest; Table 1) than the antisense strain. This demonstrates the surprising benefit of the antisense host strain for production of this plasmid even under these conditions (30° C.) wherein only low levels of RNA are produced from the temperature inducible $\lambda p_R$-$\lambda p_L$ promoters.

TABLE 1

30° C. constant temperature 10 L fed-batch fermentations with pMLV gag pol vector

| Strain | Overall plasmid yield (mg/L) | Specific plasmid yield (mg/L/OD$_{600}$) | |
|---|---|---|---|
| | | Early | Harvest |
| DH5α | 105 (172 at 37 hr) | 3.5@22 hr 2.2@35 hr 2.1@37 hr | 0.9 |
| DH5α-antisense | 197 (205 at 37 hr) | 5.8@22 hr 7.7@35 hr 7.5@37 hr 5.0@40 hr | 5.0* |
| DH5α-antisense | 206 (240 at 37 hr) | 7.8@35 hr 7.7@37 hr | 6.7* |
| DH5α-antisense | 464 (386 at 39 hr) | 4.5@39 hr | 5.1* |

*Plasmid was high quality supercoiled monomer

Example 4

Host Strain Producing Sense RNA Against Influenza H1 Ha Insert Improved Toxic Plasmid Yield When attempting to clone the H1 gene into the integration vector, unexpectedly the antisense orientation (relative to the $\lambda p_R$-$\lambda p_L$ promoters) was unclonable, while the sense orientation (pINT-PR-PL-H1 sense) was readily obtained. This demonstrates that H1 toxicity is not due to transcription of the H1 hemagglutinin gene (sense strand). Transcription of the antisense strand appears to mediate toxicity. NTC7382 41H H1 HA plasmid production in an *E. coli* DH5α host with the pINT-PR PL-H1 sense vector integrated into the phage HK022 attachment site (DH5α–pINT-PR PL-H1 sense; expresses sense RNA complementary to antisense H1 HA under heat induction) was dramatically improved compared to DH5α (Table 2). Improvement was observed both under uninduced conditions (30° C.) wherein only low levels of RNA are produced from the temperature inducible $\lambda p_R$-$\lambda p_L$ promoters and after temperature induction (42° C.) of the $\lambda p_R$-$\lambda p_L$ promoters. The improved yield is not due to a generic effect of the genomic pINT PR PL plasmid insertion, since no yield difference was observed between DH5α and NTC3012 (DH5α containing a single copy of the pAH144-Lambda Repressor zwf-lambdaR plasmid integrated into the HK022 attachment site; this vector is a protein expressing version of the pINT PR PL plasmid) with multiple plasmids including a plasmid containing the H1 insert evaluated herein (Carnes et al., Supra, 2009).

TABLE 2

30° C.-42° C. temperature induced 10 L fed-batch fermentations with NTC7382 41H H1 HA

| Strain | Final OD$_{600}$ | Overall plasmid yield (mg/L) | Specific plasmid yield (mg/L/OD$_{600}$) | |
|---|---|---|---|---|
| | | | Uninduced (30° C.) | Induction (42° C.) |
| DH5α | 81 | 108 (252 at 32 hr) | 0.6 @28 hr | 3.3 @32 hr 1.6 @35 hr 1.3 @38 hr |
| DH5α-sense** | 79 | 595 | 1.2 @28 hr | 7.5 @39 hr* |

*Plasmid was high quality supercoiled monomer
**DH5α-sense is DH5α pINT-PR PL-H1 sense Example 5

Host Strain Producing Antisense RNA Against dsRedExpress Insert Decreases Uninduced Protein Expression One application of chromosomal expression of a RNA copy of the plasmid insert gene would be to reduce leaky expression from expression vectors prior to induction. This would reduce metabolic burden during growth (due to expression of plasmid borne protein) resulting in improved plasmid stability, cell line viability, and ultimately induced protein production yield.

This was evaluated with expression vector pVEX-DsRE-DEXPRESS (FIG. 4). In this vector, DsREDExpress is under the control of the IPTG inducible tac promoter. This promoter is leaky, resulting in expression of DsREDExpress during culture growth without inducer. This is generally detrimental, since it increases plasmid mediated cell burden prior to induction. The entire dsREDExpress gene was excised from this vector with XbaI and XhoI (FIG. 4) and inserted into XbaI and SalI (sticky end is compatible with XhoI) digested pINT PR PL vector. This inserts the DsREDExpress gene in antisense orientation, such that the antisense strand is expressed from the $\lambda p_R$-$\lambda_L$ promoters. The resultant clone (pINT PR PL DsREDExpress antisense) was sequence verified, and integrated into DH5α to create a DH5α-antisense cell line (DH5α–pINT PR PL DsREDExpress antisense=DH5α-antisense) as described in Example 2. The pVEXDsREDExpress expression plasmid was transformed into both DH5α and DH5α-antisense cell lines, and the following 4 cell lines established: A) DH5α; B) DH5α-Antisense; C) DH5α-Antisense+pVEXDsREDExpress; D) DH5α+pVEXDsREDExpress. LB cultures were inoculated with cells from cell lines A-D, and grown to saturation in LB media at 30° C. or 37° C. One mL aliquots of cells were pelleted and resuspended in 150 uL of TE (10 mM Tris, 1 mM EDTA pH 8.0) buffer. Cells were lysed by sonication, and a clarified soluble lysate created by centrifugation. Fluorescence (DsREDExpress) of each lysate was determined using a Darkreader transilluminator DR-195M (Clare Chemical Research, Dolores, Colo.). The results (FIG. 5) demonstrate complete elimination of leaky uninduced DsREDExpress in the DH5α-Antisense+pVEXDsREDExpress cell line. Elimination of leaky expression was observed after growth at 30° C. (wherein only low levels of antisense RNA are produced from the temperature inducible $\lambda p_R$-$\lambda p_L$ promoters) and after growth at 37° C. (higher levels of antisense production from the temperature inducible $\lambda p_R$-$\lambda p_L$ promoters). This example demonstrates the general utility of chromosomal expression of an antisense RNA copy of an expression plasmid insert gene to reduce leaky uninduced protein expression.

These examples demonstrate the general utility, to improve plasmid yield, of chromosomal expression of a RNA copy of a plasmid insert gene. While not limiting the application of the invention, the yield improvement may be the result of expression of RNA that is complementary to plasmid borne toxic RNA.

Unlike inclusion of antisense promoters in the vector to reduce expression of sense peptides as taught by Weiner et al., Supra, 2005, the method of the invention is applicable to cases such as influenza HI wherein toxicity correlates with expression of the antisense strand. As well, the method of the invention has the advantage that it does not require alteration to the plasmid vector sequence. The DNA strand mediating toxicity may be easily identified by cloning since the orientation that expresses a toxic RNA will be unclonable in an expression vector. The complementary non-toxic orientation that can be cloned is then integrated into the genome to make a designer production host specific for the problem plasmid. Alternatively, integrated cell lines expressing either the sense or antisense strands may be created, and tested for improved target plasmid copy number and stability.

The art teaches that stabilization of a plasmid containing an insert encoded toxic peptide can be achieved through expression of high levels of antisense RNA from a second multicopy plasmid. Multicopy plasmids are required to obtain sufficiently high RNA levels for gene suppression (Futterer et al., Supra, 1988). However, inclusion of an additional RNA expressing plasmid in a strain is not desired, since the second plasmid will require selection to maintain stability, and limited host cell metabolic resources are wasted on propagating the second plasmid. The increased metabolic burden associated with maintaining a second plasmid is also undesired. As well, for plasmid production, contamination of a target plasmid with a RNA expressing second replicon would be unacceptable. Unexpectedly, we have determined that sufficient RNA expression can be obtained using a single genomic copy of an anti-insert RNA expression vector to stabilize plasmids. Plasmid stabilization was achieved even under uninduced conditions (30° C.), wherein very little anti-insert RNA is made. While the surprising basis for plasmid yield improvement is unknown, RNA expressed from the chromosome may improve yield by RNA:RNA interactions that interfere with toxic protein translation or reduce insert encoded mRNA levels through increasing RNA degradation rate by targeted degradation by dsRNA dependent RNases. Alternatively, unusual DNA structures in a vector may be stabilized by RNA:DNA interactions.

The art teaches that identification of effective antisense regulators requires undue experimentation. For example, Kemmer C. and Neubauer P. 2006. Microbial Cell Factories 5:38 teach that only $1/7$ designed antisense regulators were functional and that long antisense RNAs are not effective silencers. By contrast, the improved plasmid yield from chromosomal expression of RNAs disclosed herein was obtained after expression of the entire insert RNA. If necessary, an investigator skilled in the art could determine partial insert fragments that could be expressed from the chromosome to stabilize the corresponding plasmid.

These examples also demonstrate the general utility of chromosomal expression of an antisense RNA to reduce leaky uninduced protein expression from an expression plasmid insert gene. Subsequent induction of the strong plasmid borne promoter will override chromosomal antisense repression, and induce expression of the plasmid borne protein. This reduction in metabolic burden during growth (due to uninduced expression of plasmid borne protein) can be used to improve plasmid stability and cell line viability, ultimately resulting in improved production.

Thus, the reader will see that the anti-insert chromosomal RNA expression systems of the invention provide for a rational approach to improve stability and yield of plasmids. This has applications where the plasmid is the product (e.g. plasmid production) and where a plasmid is used to direct expression of a protein or protein operon during production of protein, RNA, nucleotides, or biosynthetic pathway products. The method of the invention is applicable to a wide range of gram negative and gram positive bacterial organisms as well as to other cells and organisms that are subject to RNA antisense regulation.

While the above description contains many specifications, these should not be construed as limitations on the scope of the invention, but rather should be viewed as an exemplification of preferred embodiments thereof. Many other variations are possible. For example, chromosomal expression of sense or antisense RNA targeting one or more phage genes may be used to confer phage immunity to the strain. This method has the advantage in that it does not require gene knockout of phage receptor genes, which may impair the host strain. For example, mutation of fhuA, the phage T1 receptor, confers resistance to phage T1 infection. However, fhuA is also a receptor for ferric hydroxamate uptake; fhuA mutations may therefore be detrimental to the host strain under metal limiting conditions. Likewise, chromosomal expression of sense or antisense RNA of transposon genes may be used to inhibit transposon mobilization.

Alternatively, inducible expression of chromosomally encoded RNA targeting an endogenous chromosomal RNA may be used to selectively alter expression levels of the target protein. As with anti-insert RNA, the art teaches antisense down regulation of chromosomal gene expression functions only when the antisense RNA is expressed from a multicopy plasmid (Coleman J, Green P J, Inouye M. 1984. Cell 37: 429-436). However, inclusion of an additional antisense expressing plasmid in a strain is not desired, since the plasmid will require selection to maintain stability, and limited host cell metabolic resources are wasted on propagating the plasmid. The chromosomal RNA expression method of the invention enables transient downregulation of one or more specific regulatory proteins, without relying on expression of one or more additional plasmids in the host cell line. As well, multiple target genes may be transiently downregulated using the chromosomal RNA expression method of the invention, from multiple integrated antisense regulators or a single integrated antisense regulator that expresses multiple RNAs, or a single chimeric RNA that is complementary to multiple cellular targets. The chromosomal RNA expression method of the invention may be used in metabolic engineering to fine tune expression levels of specific genes in natural or synthetic operons. The target RNAs for translational downregulation may be endogenous or heterologous genes, expressed from the chromosome or resident plasmid.

The antisense regulators may be integrated into the chromosome using the plurality of methods described in the art, such as at one or more bacteriophage attachment sites (Haldimann and Wanner, Supra, 2001) or any defined genomic site using gene replacement technologies, for example lambda red gam recombination (Datsenko K A, Wanner B L. 2000 *Proc Natl. Acad. Sci. U S A.;* 97:6640-6645). As well, the antisense regulators may be expressed using constitutive or inducible promoters. Constitutive promoters that are preferred include, but are not limited to, $P_{AMP}$, $P_{5/6,4/6}$, $P_{5/6,5/6}$, disclosed in Lissemore J L, Jankowski J T, Thomas C B, Mascotti D P, deHaseth P L. 2000. *Biotechniques* 28: 83-89, included herein by reference. Inducible promoters that are preferred include, but are not limited to, $\lambda p_R$-$\lambda p_L$, other phage promoters such as T5, T7, synthetic promoters such as tac and trc, endogenous promoters such as lac, cold shock promoters (cspA), araBAD, stationary phase or starvation promoters, growth rate (rmf) pH (cadA) or anoxia responsive (nar) promoters. Induction can be by increased temperature (PL, tac), decreasing temperature (cspA; cold shock promoter) with thermostable repressors (lambda repressor, lac repressor), inducers (IPTG for tac, trc and lac; Arabinose for AraBAD) or other means (e.g. entry into stationary phase, pH or oxygen shift, glucose or amino acid starvation; reviewed in: Makrides SC. 1996 *Microbiol. Rev.* 60:512-538). This allows tremendous flexibility in downregulation of the target gene by the antisense RNA. The chromosomal RNA expression method of the invention may be applied to the various applications of plasmid expressed RNA defined in the art, such as for metabolic engineering enhanced productivity of the bacterial host. Applications of antisense RNA are described in Lee L K, and Roth C M. 2003 Current Opinion Biotechnology 14:505 and Rasmussen L C V, Sperling-Petersen H U, and Mortensen K K. 2007. Microbial Cell Factories 6:24 and are included herein by reference.

Accordingly, the scope of the invention should be determined not by the embodiments illustrated, but by the appended claims.

What is claimed is:

1. A method for increasing production yield of covalently closed super-coiled plasmid DNA containing a target gene, comprising the steps of:
   a. cloning part or all of the target gene into a RNA expression vector, the RNA expression vector expressing a sense or an antisense RNA of the target gene;
   b. integrating a single copy of the RNA expression vector into the *E. coli* bacterial genome to create a modified *E. coli* bacterial cell line;
   c. transforming the plasmid into the modified *E. coli* bacterial cell line to form resultant transformed bacterial cells, wherein the modified *E. coli* contains a single chromosomal copy of the sense or the antisense RNA of the target gene acting as a regulator to generate sense or antisense RNA to effectively downregulate translation of multiple plasmid copies of the target gene, the modified *E. coli* bacterial cell line being competent for transformation; and
   d. isolating the resultant transformed bacterial cells to create a seed stock for plasmid propagation;
whereby the modified *E. coli* bacterial cell line improves the plasmid copy number in subsequent shake flask and or fermentation culture.

2. The method of claim 1 wherein the plasmid is a eukaryotic expression vector.

3. The method of claim 1 wherein the plasmid is a prokaryotic expression vector.

4. The method of claim 1 wherein the RNA expression vector expresses an antisense RNA of the target gene.

5. The method of claim 1 wherein the RNA expression vector expresses a sense RNA of the target gene.

* * * * *

SEQUENCE LISTING

```
<160> NUMBER OF SEQ ID NOS: 1

<210> SEQ ID NO 1
<211> LENGTH: 3868
<212> TYPE: DNA
<213> ORGANISM: Artificial Sequence
<220> FEATURE:
<223> OTHER INFORMATION: Description of Artificial Sequence: pINT PR PL
      vector

<400> SEQUENCE: 1
ctgcaggtga tgattatcag ccagcagaga ttaaggaaaa cagacaggtt tattgagcgc      60
ttatctttcc ctttattttt gctgcggtaa gtcgcataaa aaccattctt cataattcaa     120
tccatttact atgttatgtt ctgaggggag tgaaaattcc cctaattcga tgaagattct     180
tgctcaattg ttatcagcta tgcgccgacc agaacacctt gccgatcagc caaacgtctc     240
ttcaggccac tgactagcga taactttccc cacaacggaa caactctcat tgcatgggat     300
cattgggtac tgtgggttta gtggttgtaa aaacacctga ccgctatccc tgatcagttt     360
cttgaaggta aactcatcac ccccaagtct ggctatgcag aaatcacctg gctcaacagc     420
ctgctcaggg tcaacgagaa ttaacattcc gtcaggaaag cttggcttgg agcctgttgg     480
tgcggtcatg gaattacctt caacctcaag ccagaatgca gaatcactgg cttttttggt     540
tgtgcttacc catctctccg catcaccttt ggtaaaggtt ctaagcttag gtgagaacat     600
ccctgcctga acatgagaaa aaacagggta ctcatactca cttctaagtg acggctgcat     660
actaaccgct tcatacatct cgtagatttc tctggcgatt gaagggctaa attcttcaac     720
gctaactttg agaattttg caagcaatgc ggcgttataa gcatttaatg cattgatgcc     780
attaaataaa gcaccaacgc ctgactgccc catccccatc ttgtctgcga cagattcctg     840
ggataagcca agttcatttt tcttttttc ataaattgct ttaaggcgac gtgcgtcctc     900
aagctgctct tgtgttaatg gtttcttttt tgtgctcata cgttaaatct atcaccgcaa     960
gggataaata tctaacaccg tgcgtgttga ctatttacc tctggcggtg ataatggttg    1020
catgtactaa ggaggttgta tggaacaacg cataaccctg aaagattatg caatgcgctt    1080
tgggcaaacc aagacagcta aagatctctc acctaccaaa caatgccccc ctgcaaaaaa    1140
taaattcata taaaaaacat acagataacc atctgcggtg ataaattatc tctggcggtg    1200
ttgacataaa taccactggc ggtgatactg agcacatcag caggacgcac tgaccaccat    1260
gaaggtgacg ctcttaaaaa ttaagccctg aagaagggca gcattcaaag cagaaggctt    1320
tggggtgtgt gatacgaaac gaagcattgg gatccggata acaatttcac acaggaaaca    1380
gctatgacca tgattacgcc aagcttgcat gcctgcaggt cgactctaga ggatccccgg    1440
```

-continued

```
gtaccgagct cgaattctca tgtttgacag cttatcactg atcagtgaat taatggcgat    1500
gacgcatcct cacgataata tccgggtagg cgcaatcact ttcgtctcta ctccgttaca    1560
aagcgaggct gggtatttcc cggcctttct gttatccgaa atccactgaa agcacagcgg    1620
ctggctgagg agataaataa taaacgaggg gctgtatgca caaagcatct tctgttgagt    1680
taagaacgag tatcgagatg gcacatagcc ttgctcaaat tggaatcagg tttgtgccaa    1740
taccagtaga aacagacgaa gaagctagct aatgctctgt ctcaggtcac taatactatc    1800
taagtagttg attcatagtg actggatatg ttgcgttttg tcgcattatg tagtctatca    1860
tttaaccaca gattagtgta atgcgatgat ttttaagtga ttaatgttat tttgtcatcc    1920
tttaggtgaa taagttgtat atttaaaatc tctttaatta tcagtaaatt aatgtaagta    1980
ggtcattatt agtcaaaata aaatcatttg tcgatttcaa ttttgtccca tggctaattc    2040
ccatgtcagc cgttaagtgt tcctgtgtca ctcaaaattg ctttgagagg ctctaagggc    2100
ttctcagtgc gttacatccc tggcttgttg tccacaaccg ttaaaccttn aaagctttaa    2160
aagccttata tattctttttt tttcttataa aacttaaaac cttagaggct atttaagttg    2220
ctgatttata ttaattttat tgttcaaaca tgagagctta gtacgtgaaa catgagagct    2280
tagtacgtta gccatgagag cttagtacgt tagccatgag gtttagttc gttaaacatg    2340 agagcttagt acgttaaaca tgagagctta gtacgtgaaa catgagagct tagtacgtac    2400
tatcaacagg ttgaactgct gatcttcaga tcctctacgc cggacgcatc gtggccggat    2460
cttgcggccg ctcggcttga acgaattgtt agacattatt tgccgactac cttggtgatc    2520
tcgcctttca cgtagtggac aaattcttcc aactgatctg cgcgcgaggc caagcgatct    2580
tcttcttgtc caagataagc ctgtctagct tcaagtatga cgggctgata ctgggccggc    2640
aggcgctcca ttgcccagtc ggcagcgaca tccttcggcg cgattttgcc ggttactgcg    2700
ctgtaccaaa tgcgggacaa cgtaagcact acatttcgct catcgccagc ccagtcgggc    2760
ggcgagttcc atagcgttaa ggtttcattt agcgcctcaa atagatcctg ttcaggaacc    2820
ggatcaaaga gttcctccgc cgctggacct accaaggcaa cgctatgttc tcttgctttt    2880
gtcagcaaga tagccagatc aatgtcgatc gtggctggct cgaagatacc tgcaagaatg    2940
tcattgcgct gccattctcc aaattgcagt tcgcgcttag ctggataacg ccacggaatg    3000
atgtcgtcgt gcacaacaat ggtgacttct acagcgcgga gaatctcgct ctctccaggg    3060
gaagccgaag tttccaaaag gtcgttgatc aaagctcgcc gcgttgtttc atcaagcctt    3120
acggtcaccg taaccagcaa atcaatatca ctgtgtggct tcaggccgcc atccactgcg    3180
gagccgtaca aatgtacggc cagcaacgtc ggttcgagat ggcgctcgat gacgccaact    3240
acctctgata gttgagtcga tacttcggcg atcaccgctt ccctcatgat gtttaacttt    3300
gttttagggc gactgccctg ctgcgtaaca tcgttgctgc tccataacat caaacatcga    3360
cccacggcgt aacgcgcttg ctgcttggat gcccgaggca tagactgtac cccaaaaaaa    3420
cagtcataac aagccatgaa aaccgccact cgcgccgttac caccgctgcg ttcggtcaag    3480
gttctggacc agttgcgtga gcgcatacgc tacttgcatt acagcttacg aaccgaacag    3540
gcttatgtcc actgggttcg tgccttcatc cgtatcgatg gccccgatg gtagtgtggg    3600 gtctccccat gcgagagtag ggaactgcca ggcatcaaat aaaacgaaag gctcagtcga    3660
```

```
aagactgggc ctttcgtttt atctgttgtt tgtcggtgaa cgctctcctg agtaggacaa    3720
atccgccggg agcggatttg aacgttgcga agcaacggcc cggagggtgg cgggcaggac    3780
gcccgccata aactgccagg catcaaatta agcagaaggc catcctgacg gatggccttt    3840
ttgcgtggcc agtgccaagc ttgcatgc                                       3868
```